United States Patent [19]

Lepage et al.

[11] Patent Number: 4,605,543
[45] Date of Patent: Aug. 12, 1986

[54] PREPARATION OF SILANE FROM METHYLDICHLOROSILANE AND CHLOROSILANES

[75] Inventors: Jean-Luc Lepage, Sainte-Foy-les Lyon; Gerard Soula, Meyzieu, both of France

[73] Assignee: Rhone-Poulenc Specialities Chimiques, Courbevoie, France

[21] Appl. No.: 655,730

[22] Filed: Sep. 28, 1984

[30] Foreign Application Priority Data

Sep. 28, 1983 [FR] France ................... 83 15405

[51] Int. Cl.$^4$ .............. C01B 33/04; C01B 33/107; C07F 7/08
[52] U.S. Cl. ........................ 423/347; 423/342; 556/469
[58] Field of Search ............. 423/342, 347; 556/465, 556/469

[56] References Cited

U.S. PATENT DOCUMENTS

| | | | |
|---|---|---|---|
| 2,834,648 | 5/1958 | Bailey et al. | 423/342 |
| 2,900,225 | 8/1959 | Clasen | 556/469 |
| 3,044,845 | 7/1962 | Jex et al. | 423/342 |
| 3,322,511 | 5/1967 | Weyenberg | 423/342 |
| 3,419,354 | 12/1968 | Berger | 423/347 |
| 3,445,200 | 5/1969 | Dunogues et al. | 423/342 |
| 3,627,501 | 12/1971 | Kruger | 423/342 |
| 3,968,199 | 7/1976 | Bakay | 423/347 |
| 4,018,871 | 4/1977 | Marin et al. | 423/347 |
| 4,079,071 | 3/1978 | Neale | 423/347 |
| 4,113,845 | 9/1978 | Litteral | 423/342 |
| 4,151,114 | 4/1979 | Oswald et al. | 556/465 |
| 4,395,389 | 7/1983 | Seth | 423/347 |
| 4,405,590 | 9/1983 | Simon et al. | 423/347 |

FOREIGN PATENT DOCUMENTS

36-23171  11/1961  Japan ................... 556/469

OTHER PUBLICATIONS

Cotton et al., Advanced Inorganic Chemistry 1972, p. 628.
Specialty Chem. Products Corporation Catalogue 5/25/84.

*Primary Examiner*—Jack Cooper
*Attorney, Agent, or Firm*—Burns, Doane, Swecker & Mathis

[57] ABSTRACT

Silane, well adopted as a source of semiconductor/photovoltaic grade silicon, is facilely prepared from methyldichlorosilane and trichlorosilane and/or tetrachlorosilane by, (A) in a first step catalytically redistributing methyldichlorosilane with trichlorosilane or tetrachlorosilane, or admixture thereof, to form methyltrichlorosilane and dichlorosilane, and separating dichlorosilane from the resulting reaction medium, and (B) in a second step, catalytically disproportionating the dichlorosilane thus separated to form silane and trichlorosilane, and thence recovering silane thus formed and optionally recycling trichlorosilane to said step (A).

24 Claims, 1 Drawing Figure

PREPARATION OF SILANE FROM METHYLDICHLOROSILANE AND CHLOROSILANES

BACKGROUND OF THE INVENTION

1. Field of the Invention

Figure 1:
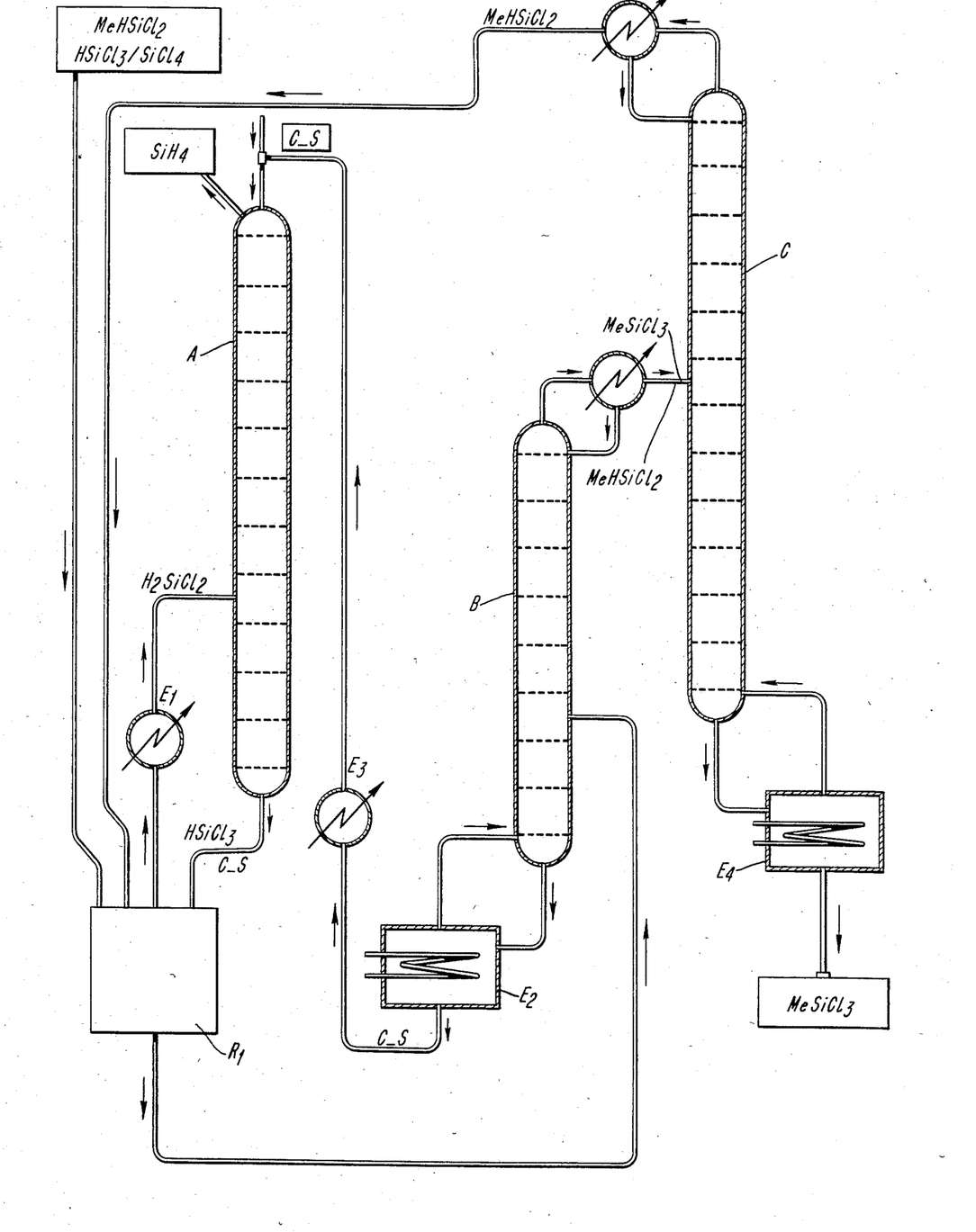

The present invention relates to the preparation of silane from methyldichlorosilane and chlorosilanes, and, more especially, to the preparation of silane from methyldichlorosilane and trichlorosilane and/or tetrachlorosilane.

2. Description of the Prior Art

Silane is a preferred raw material for producing, by decomposition, silicon of a grade which may be employed particularly in semiconductor or photovoltaic devices, e.g., solar cells.

It is known to this art to prepare silane by disproportionation of trichlorosilane in the presence of various catalysts according to the following equilibrium reactions:

$$2HSiCl_3 \rightleftharpoons H_2SiCl_2 + SiCl_4 \qquad (1)$$

$$2H_2SiCl_2 \rightleftharpoons HSiCl_3 + H_3SiCl \qquad (2)$$

$$2H_3SiCl \rightleftharpoons SiH_4 + H_2SiCl_2 \qquad (3)$$

giving, overall:

$$2HSiCl_3 \rightleftharpoons SiH_4 + 3SiCl_4 \qquad (4)$$

Thus, according to French Pat. No. 2,261,977, it has been proposed to prepare silane by disproportionation or redistribution of $HSiCl_3$ in a bed of solid anion exchange resin at a temperature which is sufficient to cause the vaporization, out of the reaction zone, of the lowest boiling reaction products and to cause the condensation of the higher boiling liquid product resulting from the reaction, $SiCl_4$, and its outflow away from the reaction zone. The temperature at the top of the bed is maintained at a level above the boiling point of $SiH_4$ and below the boiling point of $H_3SiCl$, and $SiH_4$ containing small amounts of hydrogen and chlorosilane which require a downstream separation, is recovered from the bed.

This process, which is extremely complicated and difficult to carry out, employs either a continuous distillation of the products of the various equilibrium reactions (1), (2) and (3) and permits some separation of the various products present, or employs a purification of $SiH_4$ in a charcoal trap.

Furthermore, there are also known various processes for producing dichlorosilane by disproportionation of trichlorosilane in the presence of various catalysts. Among the known catalysts for this purpose, the following have been proposed, in particular: tertiary amines of the general formula NR'R"R'" in which R', R" and R'" are identical or different alkyl radicals (French Pat. No. 1,111,925), amine hydrochlorides (French Pat. No. 2,096,605), N-substituted pyrrolidones (French Pat. No. 2,290,447) and tetraalkylureas (French Pat. No. 2,290,448).

SUMMARY OF THE INVENTION

Accordingly, a major object of the present invention is the provision of an improved process for the preparation of silane, which process is characterized in that the product silane is very easily and highly selectively prepared without the need for a series of successive distillations, as in the process according to French Pat. No. 2,261,977. The process of the invention moreover, enables the markedly efficient preparation of silane from raw materials which are readily available on an industrial scale.

Briefly, the present invention features a process for the preparation of silane from methyldichlorosilane and trichlorosilane and/or tetrachlorosilane, comprising:

(A) In a first step, catalytically redistributing methyldichlorosilane and trichlorosilane and/or tetrachlorosilane into methyltrichlorosilane and dichlorosilane;

(B) In a second step, after separation of the reaction medium, the dichlorosilane formed during the first step is disproportionated in the presence of a catalyst into silane and trichlorosilane, the product silane formed is recovered and the trichlorosilane is optionally recycled to the first step.

DETAILED DESCRIPTION OF THE INVENTION

More particularly according to the present invention, the catalyst used for the first step redistribution reaction and the second step disproportionation reaction may either be identical or different, but it is preferred to use identical catalysts; the catalysts are selected from among:

(i) quaternary ammonium salts having the formula $R'_4NY$ and quaternary phosphonium salts having the formula $R'_4PY$, in which formulae $R'$, which may be identical or different, denote a monovalent hydrocarbon radical and Y a halogen;

(ii) tertiary amines of the general formula NR'R"R'" in which R', R" and R'" are monovalent hydrocarbon radicals which may be identical or different;

(iii) ion exchange resins containing tertiary amine or quaternary ammonium groups; and (iv) catalytic systems containing an ionic inorganic salt $M^+A^-$ and a compound which complexes the $M^+$ cation of the said salt.

The various types of catalysts which may be used in the process of the invention are more fully described below.

The quaternary ammonium salts employed according to the invention have the formula $R'_4NY$ and the quaternary phosphonium salts have the formula $R'_4PY$, in which formulae $R'$, which may be identical or different, denote a monovalent hydrocarbon radical and Y a halogen.

In particular, $R'$ may be any monovalent hydrocarbon radical, for example, one of the alkyl radicals such as a methyl, ethyl, isopropyl, butyl, secondary hexyl, 2-ethylhexyl or octadecyl radical, one of the cycloalkyl radicals such as a cyclohexyl or cyclopentyl radical, one of the aliphatically unsaturated radicals such as a vinyl, allyl, hexenyl, cyclopentenyl or butadienyl radical, or one of the radicals containing aryl groups such as a phenyl, tolyl, benzyl, diphenyl or naphthyl radical.

$R'$ may also be any monovalent halohydrocarbon radical, for example, one of the haloalkyl radicals such as a 3-chloropropyl, 3,3,3-trifluoropropyl or 4-bromohexyl radical, a halocycloalkyl radical such as a bromocyclopentyl or difluorocyclohexyl radical, one of the aliphatically unsaturated radicals such as a chloroallyl or chlorocyclohexenyl radical and one of the radicals containing aryl groups such as a chlorophenyl, dibromophenyl, α,α,α-trifluorotolyl or bromonaphthyl radical.

Y may be any halogen, for example, chlorine, bromine or iodine.

The tertiary amines used in the process of the invention have the general formula NR'R"R"' in which R', R" and R"' are monovalent hydrocarbon radicals which may be identical or different.

In particular, R', R", R"' may be any alkyl, aryl, cycloalkyl, alkylaryl, alkylcycloalkyl, alkenyl or alkylene radical (when R' and R" are joined together); generally, such radicals have a number of carbon atoms which is below 22.

Exemplary of the tertiary amines which are especially preferred, representative are: tri-n-propylamine, triisopropylamine, diisopropylethylamine, tri-n-butylamine, triisobutylamine, tri-sec-butylamine, tri-n-pentylamine, di-n-butylethylamine, diisobutylethylamine, di-2-ethylbutylmethylamine, di-n-octylmethylamine, di-2-ethylhexylmethylamine, dilaurylmethylamine, triundecylamine, trioctadecylamine, n-octadecyl-n-propylethylamine, di-n-butylphenylamine, triphenylamine, tris(diphenyl)amine, 2-naphthyldi-n-butylamine, tritolylamine, trixylylamine, tris(phenylmethylphenyl)amine, tris(2-phenylethyl)amine, tris(8-phenyloctyl)amine, tricyclohexylamine, tricyclooctylamine, tris(4-methylcyclohexyl)amine, tris(2-cyclohexylethyl)amine, tris(3-n-butenyl)amine, triisobutenylamine, diallyl-n-butylamine, N-n-propylpiperidine, N-isobutylpyrrolidine, N-isobutylmorpholine, and the like.

The catalyst of the invention may also comprise an ion exchange resin which is insoluble in the reagents employed in the reaction and containing tertiary amine groups or quaternary ammonium groups in which the alkylamine or alkylammonium radicals preferably contain from 1 to 8 carbon atoms, such groups being joined via a carbon atom to the resin structure.

The catalytic system containing an ionic inorganic salt $M^+A^-$ and a compound which complexes the $M^+$ cation of said salt is such that the ionic inorganic salt $M^+A^-$ should not react with the various materials present in the reaction medium.

The ionic inorganic salts of the formula $M^+A^-$ are advantageously selected from those in which $M^+$ denotes an alkali metal, an alkaline earth metal or ammonium, and preferably: $Li^+$, $Na^+$, $K^+$, $Ca^{++}$, $NH^+_4$ and those in which $A^-$ denotes a halogen, $SCN^-$, $CN^-$, $CO^{--}_3$ and preferably $Cl^-$, $Br^-$, $I^-$, $F^-$.

Although not wishing to be bound to any particular theory, it would appear that the compound which complexes the $M^+$ cation of the ionic inorganic salt enables the solution and at least partial dissociation of the salt in the reaction medium, the catalytic activity of the $A^-$ anion thereby being greatly enhanced.

In a preferred embodiment of the invention, the compound which complexes the cation of the ionic inorganic salt is a sequestering agent of the formula $$[N-(CHR_1-CHR_2-O-(CHR_3-CHR_4-O)_n-R_5)_3] \quad (I)$$

in which n is an integer greater than or equal to 0 and less than or equal to 10 ($0 \leq n \leq 10$), $R_1$, $R_2$, $R_3$ and $R_4$, which may be identical or different, denote a hydrogen atom or an alkyl radical containing from 1 to 4 carbon atoms and $R_5$ denotes an alkyl or cycloalkyl radical containing from 1 to 12 carbon atoms, a phenyl radical or a $-C_mH_{2m}-\phi$ or $C_mH_{2m+1}-\phi-$ radical, where m ranges from 1 to 12 ($1 \leq m \leq 12$), and $\phi$ is benzene.

In a second preferred embodiment of the invention, the complexing compound is a macrocyclic polyether containing from 15 to 30 ring atoms and comprising 4 to 10 —O—X units in which X is either —CHR$_6$—CHR$_7$— or —CHR$_6$—CHR$_8$—CR$_9$R$_7$—, R$_6$, R$_7$, R$_8$ and R$_9$, which may be identical or different, being a hydrogen atom or an alkyl radical containing from 1 to 4 carbon atoms, one of the symbols X optionally being —CHR$_6$—CHR$_8$—CR$_9$R$_7$— when the —O—X units comprise the group —O—CHR$_6$—CHR$_7$—.

In a third preferred embodiment of the invention, the complexing compound is a macrocyclic or dicyclic compound of the general formulae IIa or IIb.

in which Y denotes N or P; A denotes an alkylene group containing from 1 to 3 carbon atoms; D denotes O, S or N—R$_{11}$ where R$_{11}$ denotes an alkyl radical containing from 1 to 6 carbon atoms; R$_{10}$ denotes an alkyl radical containing from 1 to 6 carbon atoms; and p, q and r, which may be identical or different, are integers ranging from 1 to 5.

In a fourth preferred embodiment of the invention, a mixture of at least two of the aforesaid complexing compounds is used.

And in a fifth preferred embodiment of the invention, the complexing compound is selected from among sequestering agents, macrocyclic polyethers (also designated "crown ethers") and macrocyclic or dicyclic compounds (also designated "cryptants"), grafted onto cross-linked organic polymer supports. These grafted complexing compounds are advantageously those described in published European Patent Application No. 46,706 in the case of the grafted sequestering agents and in the *Agnew. Chem.*, Int. Ed., Engl., 18, 421–429 (1979) in the case of crown ethers or grafted cryptants.

The grafted sequestering agents described in publishedEuropean Patent Application No. 46,706 are characterized in that they comprise a cross-linked organic polymer support and a plurality of functional groups bonded to said support, and having the general formula:

in which $R'_1$, $R'_2$, $R'_3$, $R'_4$, $R'_6$ and $R'_7$, which may be identical or different, are each a hydrogen atom or an alkyl radical containing from 1 to 4 carbon atoms, $R'_5$ and $R'_8$, which may be identical or different, denote a hydrogen atom, an alkyl or cycloalkyl radical containing from 1 to 12 carbon atoms, a phenyl radical, a $-C_{q'}H_{2q'}-\phi-$ or $C_{q'}H_{2q'+1}-\phi-$ radical with q' greater than or equal to 1 and less than or equal to approximately 12, and in which n', m', and p', which may be identical or different, are greater than or equal to 1 and less than or equal to 10.

In another preferred embodiment of the invention, a sequestering agent of the formula (I) is employed, in which $R_1$, $R_2$, $R_3$ and $R_4$ denote a hydrogen atom or a methyl radical, with $R_5$ and n being as above defined.

Exemplary such sequestering agents are:

[1] tris(3-oxabutyl)amine of the formula:

[2] tris(3,6-dioxaheptyl)amine of the formula:

[3] tris(3,6,9-trioxadecyl)amine of the formula:

[4] tris(3,6-dioxaoctyl)amine of the formula:

[5] tris(3,6,9-trioxaundecyl)amine of the formula:

[6] tris(3,6-dioxanonyl)amine of the formula:

[7] tris(3,6,9-trioxadodecyl)amine of the formula:

[8] tris(3,6-dioxadecyl)amine of the formula:

[9] tris(3,6,9-trioxatridecyl)amine of the formula:

[10] tris(3,6,9,12-tetraoxatridecyl)amine of the formula:

[11] tris(3,6,9,12,15,18-hexaoxanonadecyl)amine of the formula:

[12] tris(3,6-dioxa-4-methylheptyl)amine of the formula:

[13] tris(3,6-dioxa-2,4-dimethylheptyl)amine of the formula:

The amines which may be used are per se known to the prior art. Thus, French Pat. No. 1,302,365 describes the tertiary amines $N\!-\!(CH_2\!-\!CH_2\!-\!O\!-\!CH_3)_3$ and $N\!-\!(CH_2\!-\!CH_2\!-\!O\!-\!CH_2\!-\!CH_2\!-\!O\!-\!CH_3)_3$ prepared as byproducts of the synthesis of the corresponding primary and secondary amines, such primary and secondary amines being products useful as intermediates in the synthesis of pharmaceutical substances, corrosion inhibitors, intermediates for the synthesis of chemical products for agricultural purposes, and as emulsifiers. It will of course be appreciated that the field of application of the amines obtained in the aforesaid French Pat. No. 1,302,365, which may be the same as the amines employed in the process of the present application, is completely remote from the use intended herein.

The macrocyclic polyethers which may be used in the process of the invention are known under the general name of "crown ethers" and are described in French Patent Application No. 69/43,879 published under No. 2,026,481.

As examples of the crown ethers which may be used consistent herewith, representative are:

The macrocyclic and dicyclic compounds are described in French Patent Application No. 70/21,079 published under No. 2,052,947. As examples of such compounds useful according to this invention, representative are:

In another preferred embodiment of the invention, a supported sequestering agent is used comprising a cross-linked organic polymer support with a plurality of functional groups bonded to said support, having the general formula (III), in which $R'_1$, $R'_2$, $R'_3$, $R'_4$, $R'_6$ and $R'_7$, which may be identical or different, denote a hydrogen atom or the methyl radical and $R'_5$ and $R'_8$, which may be identical or different, denote a hydrogen atom or an alkyl radical containing from 1 to 4 carbon atoms. And in still another preferred embodiment of the invention, n', m' and p', which may be identical or different, are greater than or equal to 1 and less than or equal to 6.

Exemplary of such functional groups, those having the following formulae are representative:

-continued or $$N\begin{smallmatrix}CH_2-CH_2-O-CH_2-CH_2-O-\\CH_2-CH_2-O-CH_2-CH_2-OH\\CH_2-CH_2-O-CH_2-CH_2-O-CH_3\end{smallmatrix}$$

The support may be derived from any cross-linked organic polymer containing groups which are capable of being substituted with the functional groups of the formula (III).

Exemplary of organic polymers suitable for the present invention are polymers derived from vinylaromatic compounds, such as styrene and methylstyrene, and copolymers of vinylaromatic compounds and $C_4$–$C_6$ conjugated dienes, such as copolymers of styrene with butadiene and styrene with isoprene.

It is especially preferred consistent herewith to use polystyrene as the organic polymer, with the cross-linking agent therefor, also preferably, being divinylbenzene. The degree of cross-linking is an important factor. It is necessary, in fact, that the functional groups of the formula (III) grafted onto the polystyrene be active. For this, it is necessary that the molecules of the solvent in which the supported sequestering agent is to be employed, for those applications below described, penetrate inside the polymer. For this purpose, it is necessary that the degree of cross-linking should not be too high, such as not to prevent the entry of the solvent and reactants. It is preferred to employ a polystyrene whose degree of cross-linking with divinylbenzene is below approximately 10%. Still more preferably, the degree of cross-linking is below approximately 5%.

The group which may be substituted is preferably the chlorine or bromine atom in the chloromethyl —$CH_2Cl$ or bromomethyl —$CH_2Br$ substituent on the benzene ring of the polystyrene.

It is most preferred that the percentage of benzene rings in the polystyrene bearing a functional group be greater than 5%. Even more preferably, this percentage is above 10%.

The preferred supported sequestering agents according to the invention have the following formula:

is derived from a chloromethylated or bromomethylated polystyrene cross-linked with divinylbenzene, and having the formula:

where X denotes Cl or Br.

According to another preferred embodiment of the invention, a macrocyclic polyether or a macrocyclic or dicyclic compound is used, grafted onto a cross-linked organic polymer which comprises a polystyrene obtained by reaction of suitable amine derivative of the macrocyclic polyether or of the macrocyclic or dicyclic compound with a chloromethylated polystyrene. These preferred supported products have the following formulae:

and

The first and the second step of the process of the invention may be carried out in the presence or absence of solvent. When a third solvent is employed, the latter should meet a number of conditions: it should dissolve the original silanes; it should also be chemically inert towards the silanes which are introduced or formed.

Preferably, the material selected as solvent is, for example, chlorobenzene, orthodichlorobenzene, benzene, toluene, cyclohexane, heptane, dichloroethane, methylene chloride, dichlorobenzene, tetrahydrofuran, dioxane, and dimethoxyethane.

In the first step of the process of the invention, redistribution between methyldichlorosilane and trichlorosilane and/or tetrachlorosilane is carried out to form methyltrichlorosilane and dichlorosilane in the presence of one of the catalysts which have been described above.

The reaction temperature employed for this step ranges from $-30°$ C. to the boiling point of the reaction medium. The operation is preferably carried out at the boiling point of the reaction medium in order to permit the evolution of dichlorosilane from the reaction medium as it is formed, with the boiling point of the reaction medium typically ranging from 15° C. to 120° C., and depending, particularly, on the nature of the solvent employed and its proportion in the medium.

The pressure employed may be lower than, equal to, or greater than atmospheric pressure. The process is preferably carried out at atmospheric pressure.

In this first step, the catalyst is employed in such an amount that the molar ratio of the catalyst (or the active groups in the latter in the case of resins or supported catalytic systems) to the original silanes (methyldichlorosilane and trichlorosilane and/or tetrachlorosilane) preferably ranges from 10 to 0.0001. More preferably, this ratio ranges from 0.5 to 0.005.

The molar ratio of, on the one hand, trichlorosilane and/or tetrachlorosilane to, on the other hand, methyldichlorosilane preferably ranges from 0.05 to 5. This ratio more preferably ranges from 0.1 to 2.

The molar ratio of the solvent to all of the starting material silanes ranges from 0 to 100 and preferably ranges from 0 to 10.

In the case where the catalyst systems incorporating an ionic inorganic salt and a complexing compound are used as catalyst, the complexing compound is employed in an amount such that the molar ratio of the complexing compound (or of the active groups in the latter when it is supported) to the ionic inorganic salt preferably ranges from 0.05 to 20, and more preferably from 0.5 to 2. Moreover, the molar ratio of the ionic inorganic salt to all of the beginning silanes preferably ranges from 10 to 0.0001. Still more preferably, this ratio ranges from 0.5 to 0.001.

The first step in the process may be carried out discontinuously or continuously.

It will be appreciated that, according to the process of the invention, methyldichlorosilane is employed; nevertheless, as an alternative form, dimethylchlorosilane may be reacted in the first stage, a compound which, at present, is much more costly to use than methyldichlorosilane.

In the second step of the process of the invention, after separation of the reaction medium, the dichlorosilane formed during the first step is disproportionated to form silane and trichlorosilane in the presence of one of the catalysts which have been described above.

The separation of dichlorosilane from the reaction medium is carried out by evaporating and removing the latter, either as it is being formed, when the first step is carried out at boiling temperature, or after reaction, by heating the reaction medium. Such separation is preferably continuously employed and carried out concurrently with the formation of dichlorosilane in the reaction medium during the first step.

The dichlorosilane separated in this manner may contain small amounts of trichlorosilane and/or methyldichlorosilane, without adversely affecting its use in the subsequent steps.

The disproportionation of dichlorosilane is preferably carried out in a column in which the chlorosilanes and the catalyst and its solvent circulate in opposite directions, or countercurrently. The column head temperature ranges from −50° C. to 120° C. and preferably from −30° C. to 40° C.; the temperature at the base of the column ranges from 0° C. to 120° C. and preferably from 15° C. to 60° C., the column head temperature being below or equal to the temperature at the base of the column. The column pressure may be below, equal to or above atmospheric pressure. The operation is preferably carried out at the same pressure as that employed in the first step.

Furthermore, similar to the first step, the second step may be carried out in the presence of a solvent for the reactants, such as an aliphatic or aromatic hydrocarbon. It is thus possible to use as a solvent, for example, cyclohexane, toluene, benzene, chlorobenzene, orthodichlorobenzene, 1,1,2,2-tetrachloroethane, heptane, dichloroether, methylene chloride, tetrahydrofuran, dioxane or dimethoxyethane.

In this second step, the catalyst is employed in an amount such that the molar ratio of the catalyst (or the active groups in the latter in the case of resins or supported catalystic systems) to dichlorosilane preferably ranges from 20 to 0.0002. Still more preferably, this ratio ranges from 1 to 0.01.

The molar ratio of the solvent to dichlorosilane is preferably identical to that employed in the first step of the solvent to all of the silanes.

In the case where catalytic systems containing an ionic inorganic salt and a complexing compound are employed as catalyst, the complexing compound is employed in an amount such that the molar ratio of the complexing compound to the ionic inorganic salt preferably ranges from 0.05 to 20. Still more preferably, this ratio ranges from 0.12 to 2. Moreover, the molar ratio of the ionic inorganic salt to dichlorosilane preferably ranges from 2 to 0.0002. Still more preferable, this ratio ranges from 1 to 0.01.

The silane formed during the second step is recovered at the head of the column and the trichlorosilane exits the base of the column with the catalyst and its solvent and is recycled, if appropriate, to the first step.

Silane obtained at the head of the column may be recovered as such or separated from possible residual chlorosilanes by contacting the gaseous silane emanating from the head of the column with a solvent producing selective solvation of the chlorosilanes or by liquifying the residual chlorosilanes by cooling to a low temperature. Among the solvents permitting this selective separation of the silane formed from the other residual chlorosilanes, at least one solvent selected from among benzene, chlorobenzene and orthodichlorobenzene is used.

A preferred embodiment of the present invention will now be described, with reference to the accompanying FIGURE of Drawing.

As shown in said FIGURE of Drawing, the mixture of methyldichlorosilane and trichlorosilane/tetrachlorosilane is introduced into the redistribution reaction $R_1$ which communicates with the base of column A. The unsupported catalyst C and solvent S are also introduced at the head of column A. The reactor is maintained at atmospheric pressure and the reaction mixture in $R_1$ is heated to boiling, the catalyst C and the solvent S are transferred into the reactor $R_1$ after having traversed the column A. Dichlorosilane formed in $R_1$ is separated from the reaction medium as it is formed and is conveyed into the column A (this dichlorosilane may, without detriment, contain trace amounts of unreacted silanes which may optionally be at least partly condensed in the exchanger $E_1$ and recycled into $R_1$).

The disproportionation catalyst C and the solvent S, supplied to the head of the column A circulate countercurrently with respect to the dischlorosilane. A temperature or a temperature gradient is maintained in this column A, such that the products of the disproportionation of dichlorosilane other than $SiH_4$ remain dissolved in the liquid phase, with silane being recovered at the head of the column A. The trichlorosilane formed is recovered at the base of this column mixed with the catalyst C and the solvent S, materials which are recycled into the redistribution reactor $R_1$.

If desired, it is possible to effect the separation of the catalyst and of the solvent (CS) from the chlorosilanes (methyltrichlorosilane which is formed, methyldichlorosilane, and unreacted trichlorosilane and/or silicon tetrachloride) originating from the redistribution in reactor $R_1$. This separation is carried out by distillation in column B at the base of which the catalyst and the solvent (C—S) are collected in exchanger $E_2$, and at the head of which the mixture of chlorosilanes is collected. The catalyst and the solvent may be recycled to the head of column A after being cooled in exchanger $E_3$. The dichlorosilanes in turn may be separated by distillation in column C such as to collect at the base in exchanger $E_4$ methyltrichlorosilane, which may be valorized elsewhere, and at the head of which the other chlorosilanes which may be recycled into the redistribution reactor $R_1$.

In order to further illustrate the present invention and the advantages thereof, again with reference to the accompanying FIGURE of Drawing, the following specific example is given, it being understood that same is intended only as illustrative and in nowise limitative.

EXAMPLE

The redistribution between $CH_3SiHCl_2$ and $HSiCl_3$ was carried out in a 4-liter reactor $R_1$. Column A was a column 1.6 m long and with plates 4 cm in diameter and; the disproportionation of $H_2SiCl_2$ took place in the latter.

These reactions were carried out in the presence of the catalytic system of tris(3,6-dioxaheptyl)amine (coded TDA 1) and LiBr, in a chlorobenzene medium.

$CH_3SiHCl_2$ and $HSiCl_3$ were introduced into reactor $R_1$ at a rate of 2,700 grams/hour for $CH_3SiHCl_2$ and 500 g/h for $HSiCl_3$. A portion of these chlorosilanes were derived by recycling, after separation of the catalytic system plus solvent from the $CH_3SiCl_3$ formed.

The catalytic system, dissolved in $C_6H_5Cl$ (solvent) was introduced at the head of column A.

Its companion by weight was as follows:

| | | |
|---|---|---|
| (i) | $C_6H_5Cl$ | 91.6% |
| (ii) | TDA 1 | 6.6% |
| (iii) | LiBr | 1.8% |

Its flow rate was 1,850 g/h.

This mixture was transferred into reactor $R_1$ after having passed through the column A.

The reaction medium in reactor $R_1$ was at boiling temperature (temperature of from 70° to 75° C.). The vapor phase produced principally contained $H_2SiCl_2$, but also a little $CH_3SiHCl_2$ and $HSiCl_2$. These last two chlorosilanes were partly condensed in condenser $E_1$ and recycled. $H_2SiCl_2$ which was formed was then introduced into column A in vapor state and circulated countercurrently to the mixture of catalytic system and solvent. Its disproportionation resulted in the formation of $SiH_4$ which was evolved at the head of the column and of $HSiCl_3$ which was recycled to reactor $R_1$, in solution in chlorobenzene, with the catalytic system.

The flow rate of the silane produced in this manner was 120 grams/hour.

The condensed phase originating from reactor $R_1$ had the following composition (weight percentages):

| | | |
|---|---|---|
| (1) | $H_2SiCl_2$ | 5.1% |
| (2) | $HSiCl_3$ | 0.7% |
| (3) | $CH_3SiHCl_2$ | 26.4% |
| (4) | $CH_3SiCl_3$ | 32.8% |
| (5) | TDA 1 | 2.3% |
| (6) | LiBr | 0.6% |

This mixture was transferred to the distillation column B 1.60 m long and 8 cm in diameter, in order to separate the catalytic system dissolved in $C_6H_5Cl$ from the various chlorosilanes which had not reacted or had formed. The temperature at the head was 52° C., and that at the bottom was 131° C.

The catalytic system and the solvent exiting the base of the column were recycled to the head of the column A after passing through the condenser $E_3$ which reduced the temperature of the mixture to 0° C.

The chlorosilane mixture exiting the head of column B was conveyed to the distillation column C in order to separate the $CH_3SiCl_3$ formed from the other chlorosilanes. This column was 2 m long and 8.5 cm in diameter; $CH_3SiCl_3$ exited the base thereof.

The composition of the mixture exiting the head of the column was as follows (weight percentages):

| | | |
|---|---|---|
| (1) | $H_2SiCl_2$ | 15.7% |
| (2) | $HSiCl_3$ | 2.2% |
| (3) | $CH_3SiHCl_2$ | 82.1% |

This mixture was recycled to reactor $R_1$.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of silane from methyldichlorosilane and trichlorosilane and/or tetrachlorosilane, comprising (A) in a first step, catalytically redistributing methyldichlorosilane with trichlorosilane or tetrachlorosilane, or admixture thereof, to form methyltrichlorosilane and dichlorosilane, and separating dichlorosilane from the resulting reaction medium, and (B) in a second step, catalytically disproportionating the dichlorosilane thus separated to form silane and trichlorosilane, and thence recovering silane thus formed and optionally recycling trichlorosilane to said step (A), the step (A) and step (B) reactions being catalyzed with (i) a quaternary ammonium salt having the formula $R'_4NY$ or a quaternary phosphonium salt having the formula $R'_4PY$, in which each R', which may be identical or different, is a monovalent hydrocarbon radical and Y is halogen, (ii) a tertiary amine of the general formula NR'R''R''' in which R', R'' and R''', which may be identical or different, are monovalent hydrocarbon radicals, (iii) an ion exchange resin containing tertiary amine or quaternary ammonium groups, or (iv) a catalytic system comprising an ionic inorganic salt $M^+A^-$ and a compound which complexes the $M^+$ cation of said salt.

2. The process as defined by claim 1, wherein a catalyst (i) is employed, in which each R' is methyl, ethyl, isopropyl, butyl, secondary hexyl, 2-ethylhexyl, octadecyl, cyclohexyl, cyclopentyl, vinyl, allyl, hexenyl, cyclopentyl, butadienyl, phenyl, tolyl, benzyl, diphenyl, naphthyl, 3-chloropropyl, 3,3,3-trifluoropropyl, 4-bromohexyl, bromocyclopentyl, difluorocyclohexyl, chloroallyl, chloroallyl, chlorocyclohexenyl, chlorophenyl, dibromophenyl, $\alpha,\alpha,\alpha$-trifluorotolyl or bromonaphthyl.

3. The process as defined by claim 1, wherein the catalyst comprises tri-n-propylamine, triisopropylamine, diisopropyl-n-ethylamine, tri-n-butylamine, triisobutylamine, tri-sec-butylamine, tri-n-pentylamine, di-n-butylethylamine, diisobutylethylamine, di-2-ethylbutylmethylamine, di-n-octylmethylamine, di-2-ethylbutylmethylamine, di-n-octylmethylamine, di-2-ethylhexylmethylamine, dilaurylmethylamine, triundecylamine, trioctadecylamine, n-octadecyl-n-propylethylamine, di-n-butylphenylamine, triphenylamine, tris(diphenyl)amine, 2-naphthyldi-n-butylamine, tritolylamine, trixylylamine, tris(phenylmethylphenyl)amine, tris(2-phenylethyl)amine, tris(8-phenyloctyl)amine, tricyclohexylamine, tricyclooctylamine, tris(4-methylcyclohexyl)amine, tris(2-cyclohexylethyl)amine, tris(3-n-butenyl)amine, triisobutenylamine, diallyl-n-butylamine, N-n-propylpiperidine, N-isobutylpyrrolidine or N-isobutylmorpholine.

4. The process as defined in claim 1, wherein a catalyst (iii) is employed which is insoluble in the reaction reagents and comprises tertiary alkylamine groups or quaternary alkylammonium groups in which the alkyl radicals contain from 1 to 8 carbon atoms.

5. The process as defined by claim 1, wherein a catalyst (iv) is employed, in which $M^+$ is an alkali metal, an alkaline earth metal or ammonium, and $A^-$ is a halogen, $SCN^-$, $CN^-$ or $CO_3^{--}$.

6. The process as defined by claim 1, wherein a catalyst (iv) is employed, in which the compound complexing the cation of the ionic inorganic salt comprises a sequestering agent of the formula:

$$[N-(CHR_1-CHR_2-O-(CHR_3-CHR_4-O)_n-R_5)_3] \quad (I)$$

in which n is an integer greater than or equal to 0 and less than or equal to 10 ($0 \leq n \leq 10$), $R_1$, $R_2$, $R_3$ and $R_4$, which may be identical or different, are each a hydrogen atom or an alkyl radical containing from 1 to 4 carbon atoms and $R_5$ is an alkyl or cycloalkyl radical containing from 1 to 12 carbon atoms, a phenyl radical or a $-C_mH_{2m}-\phi$ or $C_mH_{2m+1}-\phi-$ radical, wherein m ranges from 1 to 12 ($1 \leq m \leq 12$) and $\phi$ is benzene.

7. The process as defined in claim 6, wherein the sequestering agent of the formula (I) comprises:

(i) tris(3-oxabutyl)amine of the formula:

N$-(CH_2-CH_2-O-CH_3)_3$ (ii) tris(3,6-dioxaheptyl)amine of the formula:

N$-(CH_2-CH_2-O-CH_2-CH_2-O-CH_3)_3$ (iii) tris(3,6,9-trioxadecyl)amine of the formula:

N$-(CH_2-CH_2-O-CH_2-CH_2-O-CH_2-CH_2-O-CH_3)_3$ (iv) tris(3,6-dioxaoctyl)amine of the formula:

N$-(CH_2-CH_2-O-CH_2-CH_2-C_2H_5)_3$ (v) tris(3,6,9-trioxaundecyl)amine of the formula:

N$-(CH_2-CH_2-O-CH_2-CH_2-O-CH_2-CH_2-O-C_2H_5)_3$ (vi) tris(3,6-dioxanonyl)amine of the formula:

N$-(CH_2-CH_2-O-CH_2-CH_2-O-C_3H_7)_3$ (vii) tris(3,6,9-trioxadodecyl)amine of the formula:

N$-(CH_2-CH_2-O-CH_2-CH_2-O-CH_2-CH_2-O-C_3H_7)_3$ (viii) tris(3,6-dioxadecyl)amine of the formula:

N$-(CH_2-CH_2-O-CH_2-CH_2-O-C_4H_9)_3$ (ix) tris(3,6,9-trioxatridecyl)amine of the formula:

N$-(CH_2-CH_2-O-CH_2-CH_2-O-CH_2-CH_2-O-C_4H_9)_3$ (x) tris(3,6,9,12-tetraoxatridceyl)amine of the formula:

N$-(CH_2-CH_2-O-CH_2-CH_2-O)_3-CH_3)_3$ (xi) tris(3,6,9,12,15,18-hexaoxanonadecyl)amine of the formula:

N$-(CH_2-CH_2-O-(CH_2-CH_2-O)_5CH_3)_3$ (xii) tris(3,6-dioxa-4-methylheptyl)amine of the formula:

N$-(CH_2-CH_2-OCH-(CH_3)-CH_2-O-CH_3)_3$

(xiii) tris(3,6-dioxa-2,4-dimethylheptyl)amine of the formula:

N$-(CH_2-CH-(CH_3)-OCH(CH_3)-CH_2-O-CH_3)_3$.

8. The process as defined by claim 1, wherein a catalyst (iv) is employed in which the complexing compound comprises a macrocyclic polyether containing from 15 to 30 ring atoms and 4 to 10 10—O—X units, in which X is $-CHR_6-CHR_7-$ or $-CHR_6-CHR_8-CR_9R_7-$, wherein $R_6$, $R_7$, $R_8$ and $R_9$, which may be identical or different, are each a hdyrogen atom or an alkyl radical containing from 1 to 4 carbon atoms, and wherein one of the symbols X may be $-CHR_6-CHR_8-CR_9R_7-$ when the —O—X units comprise $-O-CHR_6-CHR_7-$.

9. The process as defined by claim 8, wherein said macrocyclic polyether comprises a compound of the general formula:

10. The process as defined by claim 1, wherein a catalyst (iv) is employed, in which the complexing compound comprises a macrocyclic or dicyclic compound of the general formula IIa or IIb:

(IIa)

(IIb)

wherein Y is N or P, A is an alkylene group containing from 1 to 3 carbon atoms, D is O, S or N—$R_{11}$ where $R_{11}$ is an alkyl radical containing from 1 to 6 carbon atoms, $R_{10}$ is an alkyl radical containing from 1 to 6 carbon atoms, and p, q and r, which may be identical or different, are integers ranging from 1 to 5.

11. The process as defined by claim 10, wherein said macrocyclic or dicyclic compound comprises a compound of the general formula:

12. The process as defined by any of claims 6, 8 or 10, wherein said complexing compound comprises said sequestering agents, macrocyclic polyethers, macrocyclic or dicyclic compounds grafted onto a crosslinked organic polymer support.

13. The process as defined by claim 12, wherein said complexing compound comprises sequestering agent radicals of the general formula:

(III)

in which $R_1'$, $R_2'$, $R_3'$, $R_4'$, $R_6'$ and $R_7'$, which may be identical or different, are each a hydrogen atom or an alkyl radical containing from 1 to 4 carbon atoms, $R_5'$ and $R_8'$, which may be identical or different, are each a hydrogen atom, an alkyl or cycloalkyl radical containing from 1 to 12 carbon atoms, a phenyl radical, a —$C_{q'}H_{2q'}$—$\phi$— or $C_{q'}H_{2q'+1}$—$\phi$— radical, wherein $\phi$ is benzene, q' is greater than or equal to 1, and n', m', and p', which may be identical or different, are each greater than or equal to 1 and less than or equal to 10.

14. The process as defined in claim 13, wherein said radicals of the formula (III) comprise:

15. The process as defined by claim 12, wherein said organic polymer comprises a polymer of a vinylaromatic compound or a copolymer of a vinylaromatic compound with a $C_4$-$C_6$ conjugated diene.

16. The process as defined in claim 1, wherein the first step reaction temperature ranges from −30° C. to the boiling temperature of the reaction medium.

17. The process as defined by claim 1, wherein the catalyst is present in such amount that the molar ratio of catalyst to starting material silanes ranges from 10 to 0.0001.

18. The process as defined by claim 1, wherein the molar ratio of the trichlorosilane and/or tetrachlorosilane to the methyldichlorosilane ranges from 0.05 to 5.

19. The process as defined by claim 1, wherein at least one of said steps (A) and (B) is carried out in a solvent with the molar ratio of solvent to starting material silanes ranging from 0 to 100.

20. The process as defined by claim 19, wherein said solvent comprises cyclohexane, toluene, benzene, chlorobenzene, orthodichlorobenzene, 1,1,2,2-tetrachloroethane, heptane, dichloroether, methylene chloride, tetrahydrofuran, dioxane, or dimethoxyethane.

21. The process as defined by claim 1, wherein the dichlorosilane is separated by vaporization.

22. The process as defined by claim 1, wherein the second step (B) is carried out in a column in which the chlorosilanes and the catalyst and any solvent are in countercurrent flow, the temperature at the head of which column ranging from −50° C. to 120° C., the temperature at the base of which ranging from 0° C. to 120° C., and said head temperature being less than or equal to the base temperature.

23. The process as defined by claim 22, wherein the product silane is stripped of residual chlorosilanes by contacting the gaseous silane emanating from the head of the column with a solvent extractant or by liquefying said residual chlorosilanes therefrom.

24. The process as defined by claim 1, wherein the molar ratio of catalyst to dichlorosilane ranges from 20 to 0.0002.

* * * * *